United States Patent [19]

Wada et al.

[11] Patent Number: 4,475,002

[45] Date of Patent: Oct. 2, 1984

[54] PROCESS FOR PREPARING M-ALKYLHYDROXYBENZENE

[75] Inventors: Mitsuhiro Wada, Osaka; Seizi Maki, Hyogo, both of Japan

[73] Assignee: Taoka Chemical Company, Limited, Osaka, Japan

[21] Appl. No.: 444,696

[22] Filed: Nov. 26, 1982

[30] Foreign Application Priority Data

Nov. 27, 1981 [JP] Japan .................................. 56-191038
Dec. 23, 1981 [JP] Japan .................................. 56-210285
Jan. 7, 1982 [JP] Japan .................................. 57-1503

[51] Int. Cl.$^3$ ............................................. C07C 37/04
[52] U.S. Cl. .................................. 568/795; 568/780; 568/769
[58] Field of Search ................ 568/780, 795, 790, 769

[56] References Cited

U.S. PATENT DOCUMENTS

| 2,139,372 | 12/1938 | Navies | 568/795 |
| 2,353,237 | 7/1944 | Harris | 568/795 |
| 2,735,873 | 2/1956 | Cori | 568/795 |
| 3,465,047 | 9/1969 | Ito | 568/795 |
| 4,910,994 | 10/1975 | Block | 568/795 |

FOREIGN PATENT DOCUMENTS 823378  3/1981  U.S.S.R. ............................. 568/795

Primary Examiner—Werren B. Lone
Attorney, Agent, or Firm—Wegner & Bretschneider

[57] ABSTRACT

An improved process for preparing m-alkylhydroxybenzene which comprises heating alkylbenzene or an isomeric mixture of alkylbenzenesulfonic acid in the presence of sulfuric acid and an inorganic salt at a temperature of from 150° to 210° C. to form an isomeric mixture of alkylbenzenesulfonic acid which is rich in the m-isomer, selectively hydrolyzing the isomers of alkylbenzenesulfonic acid other than the m-isomer, and caustically fusing the unhydrolyzed alkylbenzenesulfonic acid.

8 Claims, No Drawings

PROCESS FOR PREPARING M-ALKYLHYDROXYBENZENE

The present invention relates to a process for preparing m-alkylhydroxybenzene and, in particular, to an improved, economical and industrially applicable process for preparing m-alkylhydroxybenzene.

It is well known that substantially pure m-alkylhydroxybenzene can be prepared from alkylbenzene via alkylbenzenesulfonic acid as disclosed in Japanese Patent Publn. (examined) Nos. 33192/74 and 33193/74, Japanese Patent Publn. (unexamined) No. 110638/74, etc. The known process comprises the following steps: (a) heating alkylbenzene, or an isomeric mixture of alkylbenzenesulfonic acid obtained by sulfonation of alkylbenzene with sulfuric acid at a low temperature, in the presence of sulfuric acid at a temperature of 150° to 210° C. to form an isomeric mixture of alkylbenzenesulfonic acid being rich in the m-isomer; (b) selectively desulfonating the isomers other than the m-isomer in the m-rich mixture by contacting such mixture with water, preferably steam, to hydrolyze the other isomers into alkylbenzene and sulfuric acid, and removing the alkylbenzene as an azeotropic mixture with water; (c) converting the unhydrolyzed m-isomer into an alkali salt; and (d) caustically fusing the alkali salt to form m-alkylhydroxybenzene.

However, the known process has various disadvantages. The first disadvantage is due to the fact that while the yield of the m-isomer in the sulfonation and isomerization, i.e. at the step (a), increases with the elevation of the reaction temperature, a high temperature above 190° C. causes not only rapid oxidation and decomposition but also dealkylation and tar-formation, whereby the sulfonation product becomes black and tarry. Also, the desulfonation in the step (b) requires a high reaction temperature and a long period of time, which cause the simultaneous or successive desulfonation of the m-isomer or any other side reaction and result in depression of the purity or quality of the product and of the yield of the product.

The second disadvantage is the presence of a large quantity of the inorganic salt in the conversion into the alkali salt, i.e. at the step (c), and in the caustic fusion, i.e. at the step (d). When the reaction mixture of alkylbenzene and sulfuric acid is alkalized with sodium hydroxide to convert sulfonic acid into the alkali salt, simultaneously the excessive sulfuric acid is neutralized, and the total amount of the obtained mixture is subjected to caustic fusion, stirring can not be efficiently done due to the high viscosity owing to the presence of a large quantity of sodium sulfate, and sodium sulfite as by-product loses its utility value due to contamination with sodium sulfate. If, in the above process, precipitated sodium sulfate is removed by filtration before the fusion, troublesome operations such as washing with water, concentration and refiltration are required in order to minimize the loss of the sulfonic acid which is adhered on the sodium sulfate. In order to obviate this disadvantage, it was attempted to remove the excessive sulfuric acid in the sulfonation mixture by an appropriate method. The usual removing method is the so-called "liming-sodation method" in which sulfuric acid is removed as calcium sulfate. However, this method is not advantageous from the industrial viewpoint because of costly steps such as treatment of waste calcium sulfate, concentration of sulfonate solution and consumption of high energy. Recently, there was proposed a method in which alkylbenzenesulfonic acid is extracted with a mixture of a primary, secondary, tertiary or quaternary amine and a water-immiscible organic solvent (Japanese Patent Publn. (unexamined) No. 154935/80). Again, this method is not advantageous because large quantities of the amine and solvents and costly equipments are required for the extraction of alkylbenzenesulfonic acid, though the method is useful in recovery of a dilute organic acid.

As a result of the extensive study, it was found that the aforementioned side reactions in the isomerization and desulfonation can be prevented by addition of sodium sulfate in a ratio of 1 to 5 mol % of the charged sulfuric acid before the sulfonation.

It was also found that the addition of 5 to 15 mol % of an inorganic salt such as sodium sulfate is effective to prevent the side reactions and that the excessive sulfuric acid can be easily removed after layer-formation which is effected by allowing the selectively desulfonated mixture to stand above 80° C.

According to the present invention, there is provided a process for preparing m-alkylhydroxybenzene which comprises heating alkylbenzene or an isomeric mixture of alkylbenzenesulfonic acid in the presence of sulfuric acid and an inorganic salt in an amount of 1 to 15 mol % of the sulfuric acid at a temperature from 150° to 210° C. to form an isomeric mixture of alkylbenzenesulfonic acid which is rich in the m-isomer, selectively hydrolyzing the isomers of alkylbenzenesulfonic acid other than the m-isomer, and then caustically fusing the unhydrolyzed alkylbenzenesulfonic acid. After the selective hydrolysis, the reaction mixture may be allowed to stand to form layers, from which the alkylbenzenesulfonic acid is separated and then subjected to caustic fusion.

As the alkylbenzene, there may be used the one which can provide an isomeric mixture of alkylbenzenesulfonic acid being rich in the m-isomer. Specific examples are toluene, ethylbenzene, isopropylbenzene, xylene, etc. Suitable inorganic salts are sodium sulfate (Glauber's salt), sodium hydrogen sulfate, etc.

The reaction of alkylbenzene with sulfuric acid may be conducted under a conventional condition for sulfonation in the presence of an inorganic salt. For instance, when alkylbenzene is heated with sulfuric acid in the presence of anhydrous sodium sulfate at 50° to 150° C., there is produced an isomeric mixture of alkylbenzenesulfonic acid which is, however, rich in the p-isomer. Such mixture is then converted into a mixture in which the m-isomer content is equal to or higher than the p-isomer content by heating with sulfuric acid, preferably in a sulfonic acid:sulfuric acid ratio being 2:1, at a temperature of 150° to 210° C., preferably of 180° to 210° C. Alternatively, a mixture in which the m-isomer content is equal to or higher than the p-isomer content may be produced by heating alkylbenzene with excessive sulfuric acid in the presence of an inorganic salt at a temperature of 150° to 210° C.

The sulfonated or isomerized mixture is hydrolyzed by heating with water or by steam-distillating at 120° to 180° C., preferably at 150° to 170° C., to convert selectively p-alkylbenzenesulfonic acid into alkylbenzene and sulfuric acid. Alkylbenzene is removed as an azeotropic mixture with water and used for an additional feed material or a starting material.

The hydrolyzed mixture is allowed to stand for about 0.5 to 1 hour, preferably at 80° to 150° C., to form layers of sulfonic acid and sulfuric acid, which are separated from each other. The efficiency of layer-formation and separation depend on the amount of the inorganic salt, the content of the m-isomer, the temperature, etc. In order to attain the stabilization of sulfonic acid, it is essential to add the inorganic salt in an amount of 1 to 15 mol % of charged sulfuric acid. If the inorganic salt is less than 1 mol %, the side reactions such as oxidation and decomposition can not be efficiently prevented. If the inorganic salt is more than 15 mol %, the desulfonation is prevented and the content of the p-isomer can not be decreased. The amount of inorganic salt is further limited in order to effect layer-formation. If the inorganic salt such as sodium sulfate is less than 4 mol %, sulfuric acid can not be separated because the layer-formation of the mixture does not occur at or above 80° C. The layer-formation below 80° C. is not distinct. In addition, cooling requires much time. Accordingly, when the inorganic salt is less than 4 mol %, it is advisable to fuse caustically the mixture without separating sulfuric acid, and such process is also advantageous as compared with the conventional process. When the inorganic salt is not less than 5 mol %, the hydrolyzed mixture forms easily layers of sulfuric acid and sulfonic acid by allowing to stand at 80° to 150° C.

The sulfonic acid dissolved in the sulfuric acid layer does not exceed 1% by weight. The inorganic salt dissolved in the sulfuric acid layer, which crystallizes out at the ordinarily temperature, can be easily removed by filtration and reused. The filtrate may be used for other purposes as sulfuric acid with high concentration. The inorganic salt may be added either before the sulfonation or after the sulfonation and before the isomerization. When the stabilization of the sulfonic acid only during the desulfonation is desired, the inorganic salt may be added just before the desulfonation. The layer-formation and separation of sulfuric acid can be effected only after and not before the desulfonation, even after the sulfonation or isomerization. This fact suggests that the effect of the inorganic salt on layer-formation is owing to the proportion of isomers; i.e. the effect can be obtained only in the case that the content of the m-isomer is more than a certain value.

The alkylbenzenesulfonic acid obtained by desulfonation of the isomers other than the m-isomer or separated as a layer after standing the desulfonated mixture at 80° to 150° C. is caustically fused to give the desired m-alkylhydroxybenzene. The caustic fusion may be carried out under the conventional conditions, for example, forming the alkaline metal salt with an alkali (e.g. sodium hydroxide) and fusing with sodium hydroxide.

The process illustrated above has various advantages, of which the typical one is that the amount of the alkali for neutralization is reduced and accordingly the cost is lowered, because free sulfuric acid is decreased by the layer-separation. Another advantage is that the inorganic salt formed by the neutralization does not need to separate or can be easily separated without concentration, because its amount is very small.

In the extensive study, it was observed that, when the above described process is carried out in the industrial scale, the content of the m-isomer in the desulfonated mixture somewhat decreases after the caustic fusion. It was proved that the decrease of the content of the m-isomer is due to partial desulfonation of the m-isomer and to sulfonation of the alkylbenzene by sulfuric acid. The decrease of the content of the m-isomer can be avoided by adding water immediately after the desulfonation in order to reduce the temperature and the concentration of sulfuric acid.

Therefore, according to the present invention, there is also provided a process for preparing m-alkylhydroxybenzene which comprises heating alkylbenzene or an isomeric mixture of alkylbenzenesulfonic acid in the presence of sulfuric acid and an inorganic salt at a temperature of 150° to 210° C. to form an isomeric mixture of alkylbenzenesulfonic acid which is rich in the m-isomer, selectively desulfonating the isomers of alkylbenzenesulfonic acids other than the m-isomer, adding water thereto to lower the temperature to or below 150° C. immediately after the selective desulfonation and caustically fusing the undesulfonated alkylbenzenesulfonic acid.

In this process, alkylbenzene as the starting material, conditions for sulfonation, isomerization and desulfonation and the amount of the inorganic salt are substantially the same as the previously described process. The only difference is that, in the latter process, water is poured into the desulfonation mixture in order to reduce temperature of the mixture below 150° C. as quick as possible. For this purpose, it is preferable to use water as cold as possible, such as ice or ice-water. If necessary, the outer surface of the reaction vessel may be cooled. This will be useful for decreasing the amount of water. It is preferable to reduce the temperature below 150° C. within a short period, for instance, within 1 hour and preferably half an hour. The layer-formation, neutralization and caustic fusion are substantially the same as the previously described process.

According to the processes in the present invention, the oxidative decomposition of alkylbenzenesulfonic acid is remarkably prevented and therefore the sulfonation, isomerization and desulfonation at a high temperature and for a long period can be operated without significant side reactions. The content of the m-isomer can be kept unchanged after the desulfonation and through the caustic fusion. As the result, the isomeric mixture containing more than 98% of the m-isomer can be obtained economically.

The invention will now be further illustrated by means of the following examples, which are not, however, intended to limit the scope of the invention.

EXAMPLES 1 TO 5 AND COMPARATIVE EXAMPLES 1 AND 2

In these examples and comparative examples, ethylbenzene was sulfonated with sulfuric acid in the presence of anhydrous sodium sulfate, isomerized, hydrolyzed (desulfonated), separated from excess sulfuric acid, neutralized and fused with an alkali to give m-ethylphenol. The composition of the reaction mixture in each step was examined, and the relationship with the quantity of sodium sulfate was investigated.

A four-necked flask (1 liter-volume) was charged with 98% sulfuric acid (600 g). Anhydrous sodium sulfate was added thereto with stirring in respective amounts expressed as mol % of sulfuric acid given in Table 1. To this mixture, ethylbenzene (424 g) was added over 30 minutes. The temperature of the mixture was gradually elevated to 200° C. over 2 hours, during which the evaporated water was withdrawn. The heating was continued at the same temperature with stirring for 4 hours in order to isomerize. The composition of the mixture is shown by weight % in Table 1 wherein BSA, TSA and ESA are the abbreviations of benzenesulfonic acid, toluenesulfonic acid and ethylbenzenesulfonic acid, respectively.

TABLE 1

Composition of sulfonic acids after isomerization

| Composition | Example 1 | 2 | 3 | 4 | 5 | Comparative 1 | 2 |
|---|---|---|---|---|---|---|---|
| Na$_2$SO$_4$ (mol %) | 2 | 5 | 7 | 10 | 15 | 0 | 20 |
| BSA | 2.1 | 1.1 | 0.3 | 0.3 | 0.3 | 4.8 | 0.3 |
| TSA | trace | trace | trace | trace | trace | 0.9 | trace |
| o-ESA | 2.6 | 2.6 | 2.5 | 1.5 | 1.7 | 2.5 | 2.7 |
| m-ESA | 52.8 | 53.4 | 55.5 | 58.5 | 57.3 | 44.7 | 51.8 |
| p-ESA | 41.5 | 41.0 | 41.1 | 39.2 | 40.4 | 44.9 | 44.9 |
| Remainder | 1.0 | 0.8 | 0.6 | 0.5 | 0.3 | 2.2 | 0.3 |

The isomerized mixture was cooled to 170° C. Water (1100 ml) was dropped at a uniform rate into the stirred mixture at the same temperature over 10 hours in order to hydrolyze. The obtained reaction mass was left to stand at 150° C. for 30 minutes to form layers. The layer of sulfonic acids was separated. The composition in weight % of the sulfonic acids layer and the cutting percentage of sulfuric acid are shown in Table 2 wherein BSA, TSA and ESA have the same meaning as those in Table 1. In the cases that the amount of sodium sulfate was 0 and 2 mol %, there were not formed layers even at 80° C., and accordingly the cutting percentage of sulfuric acid was 0.

TABLE 2

Composition of sulfonic acids after desulfonation and cutting percentage of sulfuric acid

| Composition | Example 1 | 2 | 3 | 4 | 5 | Comparative 1 | 2 |
|---|---|---|---|---|---|---|---|
| Na$_2$SO$_4$ (mol %) | 2 | 5 | 7 | 10 | 15 | 0 | 20 |
| BSA | 2.3 | 1.8 | 1.0 | 1.1 | 1.1 | 7.0 | 1.1 |
| TSA | trace | trace | trace | trace | trace | 1.0 | trace |
| o-ESA | 1.8 | 1.7 | trace | 0.8 | 0.2 | 1.5 | 1.8 |
| m-ESA | 92.3 | 93.1 | 97.4 | 95.7 | 94.8 | 83.6 | 90.1 |
| p-ESA | 1.8 | 1.7 | 1.5 | 2.3 | 3.8 | 3.4 | 3.5 |
| Remainder | 1.7 | 1.6 | 0.1 | 0.1 | 0.1 | 3.5 | 3.5 |
| Cutting percentage of H$_2$SO$_4$ | 0 | 57 | 64 | 67 | 72 | 0 | 38 |

The separated sulfonic acid layer was neutralized to pH 8 with 50% potassium hydroxide to form a slurry, which was added dropwise to a mixture of sodium hydroxide (282 g) and potassium hydroxide (42 g) mutually melting at 330° C. The mixture was heated to 340° C. and maintained with stirring at this temperature for 1 hour. Then, the mixture was dissolved in water (1000 ml) and neutralized to pH 7.2 with 35% hydrochloric acid.

The produced phenols were extracted with ether, distilled, and further fractionally distilled. The composition in weight % of phenols and the yield of ethylphenol based on consumed ethylbenzene are shown in Table 3 wherein PH, CR and EP are the abbreviations of phenol, cresol and ethylphenol, respectively.

TABLE 3

Composition of phenols after caustic fusion and yield of ethylphenol based on consumed ethylbenzene

| Composition | Example 1 | 2 | 3 | 4 | 5 | Comparative 1 | 2 |
|---|---|---|---|---|---|---|---|
| Na$_2$SO$_4$ (mol %) | 2 | 5 | 7 | 10 | 15 | 0 | 20 |
| PH | 2.8 | 2.6 | 2.6 | 1.1 | 1.3 | 4.2 | 1.3 |
| CR | 0.3 | 0.3 | 0.5 | 0.3 | 0.3 | 1.7 | 0.3 |
| o-EP | 1.2 | 0.7 | 0.4 | 0.9 | 1.5 | 1.6 | 1.8 |
| m-EP | 93.0 | 93.9 | 93.8 | 94.3 | 92.8 | 83.4 | 91.2 |
| p-EP | 1.9 | 1.7 | 2.1 | 2.6 | 4.1 | 4.6 | 4.6 |
| High b.p. substance | 0.8 | 0.8 | 0.6 | 0.8 | trace | 4.5 | 0.8 |
| Yield (%) | 71.0 | 72.0 | 71.0 | 72.0 | 71.0 | 48.0 | 71.0 |

It can be clearly seen from above Examples and Comparative Examples that, when ethylbenzene is sulfonated in the presence of sodium sulfate, the production of toluenesulfonic acid and other impurities is decreased and ethylphenol is obtainable in high yield and high purity, as compared with the case in the absence of sodium sulfate. Accordingly, it can be said that the presence of sodium sulfate in the amount of 1 to 15 mol % of charged sulfuric acid contributes in stabilization of ethylbenzenesulfonic acid and prevention of side reactions. When, however, the amount of sodium sulfate is less than 2 mol %, the formation of layers can not be attained, and sulfuric acid can not be separated, though the prevention of side reactions is recognized. The formation of layers is observed from about 4 mol % of sodium sulfate. When the amount of sodium sulfate exceeds 15 mol %, the hydrolysis (i.e. desulfonation) is inhibited, the concentration of the p-isomer increases, and the boundary surface between the sulfonic acid layer and sulfuric acid layer becomes unclear.

EXAMPLE 6

A four-necked flask (2 liters-volume) was charged with 98% sulfuric acid (1200 g). Anhydrous sodium sulfate (102 g, 6 mol %) and then ethylbenzene (424 g) were added thereto in 30 minutes while stirring. Temperature was gradually elevated to 200° C. over 2 hours while evaporated water was withdrawn. The heating was continued with stirring for 4 hours at the same temperature in order to isomerize. Then, the mixture was cooled to 170° C. Water (2000 g) was dropped at a uniform rate into the stirred mixture at the same temperature over 10 hours in order to hydrolyze. The obtained reaction mass was left to stand at 150° C. for 30 minutes to form layers. The layer of sulfuric acid (854 g) was removed. The layer of sulfonic acid (1074 g) was neutralized to pH 7.8 with 50% potassium hydroxide and added dropwise to a mixture of sodium hydroxide (563 g) and potassium hydroxide (83 g) mutually melting at 330° C. in a 2 liter reaction vessel. The mixture was heated to 340° C. and maintained with stirring at this temperature for 1 hour. Then, the mixture was dissolved in water (2000 ml) and neutralized to pH 7.2 with 35% hydrochloric acid. The produced phenols were extracted with ether and distilled to give crude m-ethylphenol (348 g, 71% yield based on consumed ethylbenzene), which showed a purity of 98.2% after fractional distillation.

EXAMPLE 7

A 1-liter flask was charged with 98% sulfuric acid (1090 g), and anhydrous sodium sulfate (103 g, 6.7 mol %) was added thereto. Then, toluene (503 g) was added thereto in 30 minutes while stirring. Temperature was gradually elevated to 195° C. over 2 hours. The heating was continued with stirring for 4 hours at the same temperature in order to isomerize. Then, the mixture was cooled to 165° C. Water (1000 g) was dropped at a uniform rate into the stirred mixture at the same temperature over 10 hours, during which toluene (216 g) was distilled out with vaporous water. After hydrolysis, the obtained mass was left to stand at 150° C. for 30 minutes to form layers. The layer of sulfuric acid (695 g) was removed from the layer of sulfonic acid (1040 g). The latter was, as in Example 6, neutralized with 50% potassium hydroxide, caustically fused, post—treated and fractionally distilled to give m-cresol (242 g) of 98% purity.

EXAMPLE 8

A 3-liter flask was charged with 98% sulfuric acid (1700 g). Anhydrous sodium sulfate (120 g, 5 mol %) and then m-xylene (1100 g) were added thereto while stirring. Temperature was elevated to 180° C. over 2.5 hours. The heating was continued at 175°–180° C. for 3 hours in order to isomerize. Then, the mixture was cooled to 150° C. Water (700 g) was dropped continuously into the mixture at the same temperature over 3 hours. The obtained mass was left to stand for 1 hour to form layers of sulfonic acid (2334 g) and sulfuric acid (760 g, 60% in concentration) which were separated with each other. During the operation, m-xylene (270 g) was recovered. The layer of sulfonic acid was, as in Example 6, neutralized, caustically fused and post-treated to give 3,5-xylenol (707 g) of 97% purity.

EXAMPLE 9

A 6000-liter reaction vessel was charged with 98% sulfuric acid (3600 kg), and anhydrous sodium sulfate (60 kg) was added. Then, ethylbenzene (2544 kg) was added dropwise to the mixture with stirring over 1 hour. Temperature of the mixture was gradually elevated to 200° C. over 2 hours while evaporated water was withdrawn. The heating was continued at the same temperature for 4 hours in order to isomerize. Then, the mixture was cooled to 170° C. Steam (corresponding to 7800 liters of water) was blown continuously into the stirred mixture at the same temperature over 12 hours in order to hydrolyze, whereby ethylbenzene (1260 kg) was recovered. The ratio of m-isomer to p-isomer (hereinafter referred to as "m/p ratio") of ethylbenzenesulfonic acid in the desulfonated reaction mass was 97.0/3.0. The concentration of sulfuric acid in the water-sulfuric acid system (excluding ethylbenzenesulfonic acid) in the same mass was 63%.

The mass, after taking up the samples for analysis and subsequent experiment, was cooled from the outside. Simultaneously, water (500 liters) was poured into the mass over 30 minutes in order to cool and dilute the mass. The obtained mass, temperature of which was 130° C., had an m/p sulfonic acid ratio of 95.9/4.1 and a sulfuric acid concentration of 56%. The mass was neutralized to pH 8 with 47% sodium hydroxide. Sodium sulfate was removed by filtration at 80° C. The filtrate was added dropwise to a mixture of sodium hydroxide (1709 kg) and potassium hydroxide (250 kg) mutually melting at 330° C. in a 6000 liter fusing vessel. The mixture was heated to 340° C. and maintained with stirring at this temperature for 1 hour. Then, the mixture was dissolved in water (6000 liters) and neutralized to pH 7.2 with 35% hydrocloric acid. The produced phenols were separated and distilled to give crude m-ethylphenol of 94.1% purity, which gave on fractional distillation m-ethylphenol of 97.9% purity. The yield of m-ethylbenzene was 70% on the basis of consumed ethylbenzene.

COMPARATIVE EXAMPLE 3

A sample taken out in 1/1000 scale from the hydrolyzed mass in Example 9 was cooled to 130° C. over 4 hours only from the outside and without adding water. The obtained sulfonic acid had an m/p ratio of 91.5/8.5. After treating in a manner similar to that in Example 9, there was obtained crude m-ethylphenol of 90.5% purity, which gave on fractional distillation m-ethylphenol of 94.1% purity.

EXAMPLES 10 TO 12

To samples taken out in 1/1000 scale from the hydrolyzed mass in Example 9 was added water in order to attain the concentrations of sulfuric acid (in the water-sulfuric acid system) as shown in Table 4, and the mixtures were maintained at the temperatures as shown in Table 4. After the reaction, the m/p ratio of the obtained sulfonic acids was determined to give the values as shown in Table 4. Also, the purity of m-ethylphenol obtained by fusing and post-treating according to Example 9 is shown in Table 4.

COMPARATIVE EXAMPLES 4 TO 6

Samples taken out in 1/1000 scale from the hydrolyzed mass in Example 9 were maintained without adding water thereto at the temperature as shown in Table 4, and the m/p ratio of the sulfonic acid and the purity of m-ethylphenol were determined to give the values as shown in Table 4.

TABLE 4

| | Composition of sulfonic acid and purity of m-ethylphenol | | | |
|---|---|---|---|---|
| | | | m/p ratio | | Purity of m-ethyl- |
| Example | Temperature (°C.) | $H_2SO_4$ (%) | End of reaction | After 4 hrs | phenol (%) |
| 10 | 150 | 57 | 97.0/3.0 | 96.6/3.4 | 97.5 |
| 11 | 150 | 52 | 97.0/3.0 | 96.7/3.3 | 98.1 |
| 12 | 130 | 52 | 97.0/3.0 | 97.0/3.0 | 98.4 |
| Comparative | | | | | |
| 4 | 170 | 63 | 97.0/3.0 | 91.5/8.5 | 92.5 |
| 5 | 150 | 63 | 97.0/3.0 | 93.1/6.9 | 93.2 |
| 6 | 130 | 63 | 97.0/3.0 | 96.3/3.7 | 96.5 |

It can be clearly seen from the results in Examples 10 to 12 and Comparative Examples 4 to 6 that, when the hydrolyzed (i.e. desulfonated) products are allowed to stand at a temperature which is the same as or slightly lower than the hydrolyzing temperature, the hydrolysis of m-isomer proceeds further with the increase of the p-isomer. Also, it can be seen that the side reaction can be prevented to a certain extent by rapid cooling without adding water (Comparative Example 6); however, slow cooling (Comparative Example 3) is quite ineffective even though the temperature is lowered finally to 130° C. Rapid cooling with adding water is significantly effective despite the temperature is 150° C. which is higher than 130° C.

EXAMPLE 13

A 3000-liter reaction vessel was charged with toluene (1509 kg). Anhydrous sodium sulfate (140 kg) was added to the toluene. Then, 98% sulfuric acid (3270 kg) was added dropwise to the mixture with stirring over 1 hour. Temperature of the mixture was elevated to 190° C. over 2 hours. The heating was continued at 185° to 190° C. for 4 hours in order to isomerize. Then, the mixture was cooled to 160° C. Steam (corresponding to 3000 liters of water) was blown continuously at a uniform rate into the mixture over 10 hours maintained at 160°-165° C. to hydrolyze p-toluenesulfonic acid into sulfuric acid and toluene. The toluene (741 kg) was recovered azeotropically with water.

The hydrolyzed mass, which has an m/p sulfonic acid ratio of 96.8/3.2, was immediately cooled from the outside and simultaneously diluted with water (250 liters) over 30 minutes, whereby the temperature was lowered to 120° C. The m/p ratio (96.4/3.6) was practically unchanged. The cooled mass was neutralized with 47% sodium hydroxide, fused and post-treated according to Example 9 to give m-cresol (584 kg) of 98.2% purity.

COMPARATIVE EXAMPLE 7

Example 13 was substantially repeated except that cooling was effected only from the outside; i.e. dilution with water was not done. The time for cooling took 3 hours. As the result, m-cresol (574 kg) of 94% purity was obtained.

EXAMPLE 14

A 6000-liter reaction vessel was charged with 98% sulfuric acid (3600 kg), and sodium sulfate (306 kg, 6 mol %) was added with stirring. Then, ethylbenzene (2544 kg) was added to the mixture over 1 hour. Temperature of the mixture was gradually elevated to 200° C. in 2 hours while evaporated water was withdrawn. The heating was continued with stirring at the same temperature for 4 hours in order to isomerize. Then, the mixture was cooled to 170° C. Steam (corresponding to 6000 liters of water) was blown at a uniform rate into the mixture over 10 hours. The mixture was cooled from the outside and simultaneously diluted with water (500 liters) over 30 minutes, whereby the temperature was lowered to 130° C. The mixture, in which m/p ratio was 96.0/4.0, was left to stand at 130° C. for 30 minutes to form layers of sulfonic acid and sulfuric acid. The sulfonic acid layer was separated and neutralized to pH 7.8 with 50% potassium hydroxide, and the neutralized solution was added dropwise to a mixture of sodium hydroxide (1700 kg) and potassium hydroxide (250 kg) mutually melting at 330° C. in a 6000-liter fusing vessel. The mixture was heated to 340° C. and maintained at the same temperature for 1 hour. Then, the mixture was dissolved in water (6000 liters) and neutralized to pH 7.2 with 35% hydrochloric acid. The separated oil was distilled to give crude m-ethylphenol (1044 kg, yield, 71% on the basis of consumed ethylbenzene), which gave on fractional distillation m-ethylphenol of 98.0% purity.

What is claimed is:

1. A process for preparing m-alkylhydroxybenzene which comprises heating alkylbenzene or an isomeric mixture of alkylbenzenesulfonic acid in the presence of sulfuric acid and an inorganic salt selected from the group consisting of sodium sulfate and sodium hydrogen sulfate at a temperature of from 150° to 210° C. to form an isomeric mixture of alkylbenzenesulfonic acid which is rich in the m-isomer, selectively hydrolyzing the isomers of alkylbenzenesulfonic acid other than the m-isomer by heating with water or by steam distillation, and caustically fusing the unhydrolyzed alkylbenzenesulfonic acid.

2. The process according to claim 1, wherein the inorganic salt is used in an amount of 1 to 15 mol % of the sulfuric acid.

3. The process according to claim 1, wherein the unhydrolyzed alkylbenzenesulfonic acid is separated after forming layers by allowing the reaction mixture obtained in the selective hydrolysis to stand.

4. The process according to claim 3, wherein the layer-forming and separating are carried out at a temperature between 80° and 150° C.

5. A process for preparing m-alkylhydroxybenzene which comprises heating alkylbenzene or an isomeric mixture of alkylbenzenesulfonic acid in the presence of sulfuric acid and an inorganic salt selected from the group consisting of sodium sulfate and sodium hydrogen sulfate at a temperature of from 150° to 210° C. to form an isomeric mixture of alkylbenzenesulfonic acid which is rich in the m-isomer, selectively hydrolyzing the isomers of alkylbenzenesulfonic acid other than the m-isomer by heating with water or by steam distillation, adding water thereto to lower the temperature below 150° C. and caustically fusing the unhydrolyzed alkylbenzenesulfonic acid.

6. The process according to claim 5, wherein the inorganic salt is used in an amount of 1 to 15 mol % of the sulfuric acid.

7. The process according to claim 5, wherein the unhydrolyzed alkylbenzenesulfonic acid is separated after forming layers by allowing the reaction mixture obtained in the selective hydrolysis to stand.

8. The process according to claim 7, wherein the layer-forming and separating are carried out at a temperature between 80° to 150° C.

* * * * *